United States Patent [19]

Buckle et al.

[11] 4,065,457
[45] Dec. 27, 1977

[54] 4-HYDROXY-3-NITRO-CARBOSTYRIL COMPOUNDS

[75] Inventors: Derek Richard Buckle, Redhill; Barrie Christian Charles Cantello, Horsham; Harry Smith, Maplehurst near Horsham, all of England

[73] Assignee: Beecham Group Limited, Great Britain

[21] Appl. No.: 715,501

[22] Filed: Aug. 18, 1976

Related U.S. Application Data

[63] Continuation of Ser. No. 469,623, May 13, 1974, abandoned.

[30] Foreign Application Priority Data

May 19, 1973 United Kingdom ............... 24000/73
May 22, 1973 United Kingdom ............... 24317/73

[51] Int. Cl.² .......................................... C00D 215/22
[52] U.S. Cl. .......................... 260/289 K; 260/283 R; 260/288 CE; 424/258
[58] Field of Search ......... 260/289 K, 283 NT, 268 R

[56] References Cited

U.S. PATENT DOCUMENTS

| 3,025,299 | 3/1962 | Pfister et al. | 260/289 K |
| 3,271,403 | 9/1966 | Grüssner et al. | 260/289 K |
| 3,355,278 | 11/1967 | Weil et al. | 260/289 K |
| 3,836,657 | 9/1974 | Sharp | 260/289 K |
| 4,006,237 | 2/1977 | Buckle et al. | 424/258 |

FOREIGN PATENT DOCUMENTS

| 205,502 | 10/1959 | Austria | 260/289 K |
| 2,009,119 | 1/1970 | France | 260/289 K |
| 2,229,414 | 5/1974 | France | 260/289 K |
| 326,398 | 5/1929 | United Kingdom | 260/289 K |

OTHER PUBLICATIONS

Gabriel; Chem. Ber., vol. 51, pp. 1500–1515, (1918).

*Primary Examiner*—Donald G. Daus
*Assistant Examiner*—Mary C. Vaughn
*Attorney, Agent, or Firm*—Jacobs & Jacobs

[57] ABSTRACT

A class of 4-hydroxy-3-nitrocarbostyril derivatives are useful in the inhibition of certain types of antigen antibody reactions.

6 Claims, No Drawings

4-HYDROXY-3-NITRO-CARBOSTYRIL COMPOUNDS

CROSS REFERENCE

This is a continuation of Ser. No. 469,623 filed May 13, 1974, now abandoned.

This invention relates to pharmaceutical compositions which are useful in the inhibition of the effects of certain types of antigen-antibody reactions, and are therefore of value in the prophylaxis and treatment of diseases associated with allergic or immunological reactions, e.g. certain types of asthma and hay-fever and also in the treatment of rhinitis. The invention also includes a number of new 4-hydroxy-3-nitrocarbostyril derivatives and a method for their preparation.

We have discovered that certain 4-hydroxy-3-nitrocarbostyrils have useful activity in mammals in that they inhibit the effects of certain types of antigen-antibody reactions. In particular, they appear to inhibit the release of mediator substances, such as histamine, which are normally released after antigen-antibody combinations and which appear to mediate the allergic response. The class of compounds which we have found to be active in this way has formula (I).

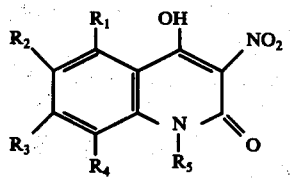

and the salts of compounds (I) are also active. In formula (I) $R_1$, $R_2$, $R_3$ and $R_4$ are each hydrogen or alkyl, alkoxy, aryloxy, aralkoxy, aryl, aralkyl, heterocyclic, hydroxy, nitro, or halogen groups or any two of the groups $R_1$, $R_2$, $R_3$ and $R_4$ taken together with the carbon atoms to which they are attached complete a substituted or unsubstituted carbocyclic or heterocyclic ring system, and $R_5$ represents hydrogen or an alkyl, aryl or aralkyl group. However, a search of the chemical literature has revealed that not all the members of class (I) are novel compounds.

Below are listed the compounds of formula (I) which have been found in the literature, together with the appropriate literature reference.

4-hydroxy-3-nitrocarbostyril[1]
3,6-dinitro-4-hydroxycarbostyril[2]
4-hydroxy-3,6,8-trinitrocarbostyril[2]

References

1. Gabriel, chem. Ber. (1918(, 51, 1500;
2. Ashley et. al., J. Chem. Soc., (1930), 382;

Although the above compounds have been reported in the literature, no form of useful biological activity has been ascribed to them. Likewise there has been in the literature, no suggestion that such compounds are likely to possess any form of useful biological activity and in particular the discovery that they have anti-allergic activity has not been predicted in any way.

Accordingly, in its broadest aspect, the present invention provides a pharmaceutical composition having anti-allergy activity comprising a compound of formula (I) or a pharmaceutically acceptable salt thereof:

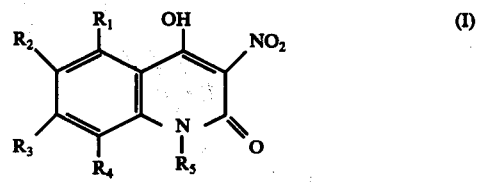

together with one or more pharmaceutically acceptable carriers, in which formula $R_1$, $R_2$, $R_3$ and $R_4$ represent hydrogen or alkyl, alkoxy, aryloxy, aralkoxy, aryl, aralkyl, heterocyclic, hydroxy, nitro, or halogen groups or any two of the groups $R_1$, $R_2$, $R_3$, and $R_4$ taken together with the carbon atoms to which they are joined complete a substituted or unsubstituted carbocyclic ring and $R_5$ represents hydrogen or an alkyl, aryl or aralkyl group, said composition being adapted for administration to human beings.

Examples of groups $R_1$, $R_2$, $R_3$ and $R_4$ which may be present in compounds (I) include hydrogen; lower alkyl groups such as methyl, ethyl, n- and iso-propyl, n-, sec- and tert - butyl, methoxy, ethoxy, n-, and iso-propoxy, n-, sec- and tert - butoxy or phenoxy, benzyloxy, phenyl, benzyl, pyridyl, fluoro, chloro, bromo, iodo. In addition $R_1$ and $R_2$ and $R_3$ or $R_3$ and $R_4$ taken together with the carbon atoms to which they are attached may form a fused phenyl or fused 1,2-cyclohexenylene ring which may carry one or more of the substituents listed above.

Preferably $R_1$ is hydrogen and $R_2$, $R_3$ and $R_4$ are each hydrogen, methyl, ethyl, n-propyl, methoxy, ethoxy or n-propoxy groups.

Similarly, examples of the group $R_5$ present in compounds (I) include hydrogen; lower alkyl groups such as those mentioned with reference to groups $R_1$–$R_4$ alone; phenyl or benzyl.

In this specification the term 'lower' means that the group to which it refers has from 1 to 6 carbon atoms.

Examples of suitable salts of compounds of formula (I) include the alkali metal salts, particularly potassium and sodium, and the alkaline earth metal salts such as aluminium and magnesium salts, as well as salts with organic bases such as amines or amino compounds.

4-Hydroxy-3-nitrocarbostyrils may exist in a number of tautomeric forms:

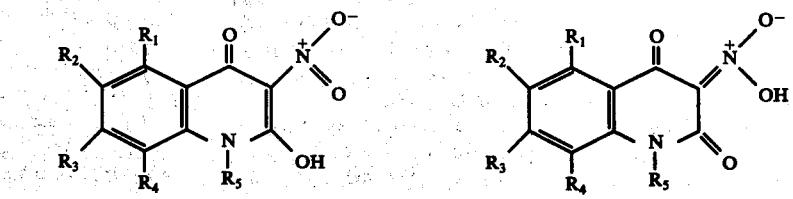

-continued

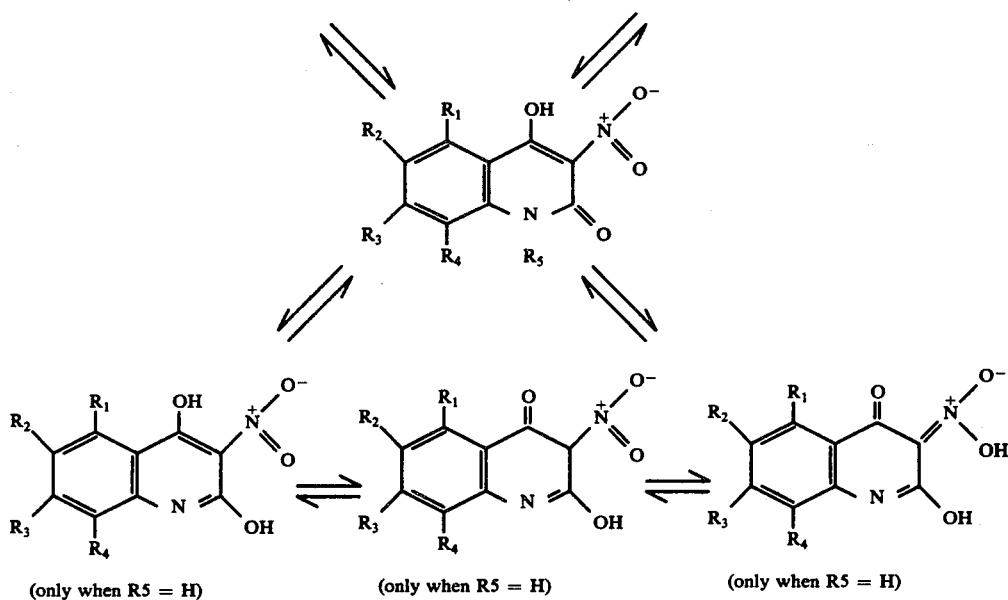

(only when R5 = H)  (only when R5 = H)  (only when R5 = H)

and it is to be understood that wherever in this specification we refer to 4-hydroxy-3-nitrocarbostyrils we also intend to include tautomeric forms of these compounds.

The compositions of this invention may be presented as a microfine powder for insufflation, e.g. as a snuff or in capsules of hard gelatin. In such a case the particles of active compound suitably have diameters of less than 50 microns, preferably less than 10 microns. Compositions may also be presented with a sterile liquid carrier for injection. Compounds of formula (I) which are active when given by the oral route, may be compounded in the form of syrups, tablets, capsules, pills and the like. Preferably the compositions are in unit dosage form, or in a form in which the patient can administer to himself a single dosage. For example when the composition is in the form of a tablet, pill, linguet, powder, troche or lozenge, any suitable pharmaceutical carrier may be used for formulating solid compositions such as, for example magnesium stearate, starch, lactose, glucose, sucrose, rice flour, talc and chalk. The composition may also be in the form of an ingestible capsule (e.g. of gelatin) to contain tne compound; or in the form of a syrup, a liquid solution or a suspension. Suitable liquid pharmaceutical carriers include ethyl alcohol, glycerine, saline and water together with flavouring or colouring agents to form syrups. A suitable dosage unit might contain from 1 to 500 mg. of active ingredient. If desired a small amount of bronchodilator compound such as isoprenaline may be incorporated into the compositions of this invention both to inhibit the cough response if the composition is insufflated and to provide immediate relief during an asthmatic attack. The effective dose of compound (I) depends on the particular compound employed, but is in general in the range of from 0.1 mg/kg/day to 100 mg/kg/day.

As is common practice, the compositions will usually be accompanied by written or printed directions for use in the medical treatment concerned, in this case as an anti-alllergic agent for prophylaxis treatment of, for example, asthma, hay-fever or rhinitis.

Most of the compounds defined above with respect to formula (I) are novel compounds. Accordingly the present invention includes within its scope compounds of formula (I) and pharmaceutically acceptable salts thereof, provided that:

a. $R_1$, $R_2$, $R_3$, $R_4$ and $R_5$ are not all hydrogen,
b. $R_2$ is not a nitro group when $R_1$, $R_3$, $R_4$ and $R_5$ are all hydrogen; and
c. $R_2$ and $R_4$ are not both a nitro group when $R_1$, $R_3$ and $R_5$ are all hydrogen.

A preferred class of novel compounds of the invention are those of formula (IA) and pharmaceutically acceptable salts thereof:

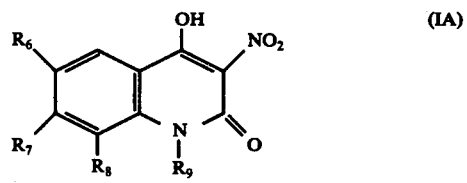

(IA)

wherein $R_6$, $R_7$, $R_8$ are each hydrogen or a lower alkyl or lower alkoxy group, and $R_9$ is hydrogen or a lower alkyl group.

Preferably one of the groups $R_6$, $R_7$ and $R_8$ are hydrogen and the other two are a methyl, ethyl, n-propyl, methoxy, ethoxy or n-propoxy group, and $R_9$ is hydrogen or a lower alkyl group.

Compounds of formula (IA) which are particularly preferred include the following and their pharmaceutically acceptable salts
6,7-dimethyl-4-hydroxy-3-nitrocarbostyril;
6,7-diethyl-4-hydroxy-3-nitrocarbostyril;
7,8-dimethyl-4-hydroxy-3-nitrocarbostyril;
4-hydroxy-8-methyl-3-nitrocarbostyril;
6-ethyl-4-hydroxy-3-nitrocarbostyril;
4-hydroxy-1,6,7-trimethyl-3-nitrocarbostyril;
6,7-diethyl-4-hydroxy-1-methyl-3-nitrocarbostyril;
4-hydroxy-3-nitro-1,7,8-trimethyl-carbostyril;
1,8-dimethyl-4-hydroxy-3-nitrocarbostyril
6-ethyl-4-hydroxy-1-methyl-3-nitrocarbostyril;

Compounds of formula (I) and, of course, formula (IA) may be prepared by nitration of the corresponding 4-hydroxycarbostyril (II) or (IIA)

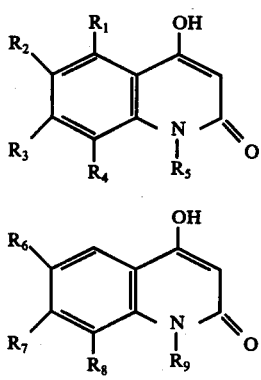

(II)

(IIA)

wherein $R_1$, $R_2$, $R_3$, $R_4$ and $R_5$ are as defined in formula (I) and $R_6$, $R_7$, $R_8$ and $R_9$ are as defined in formula (IA). Nitration may be effected using one of the following nitrating agents:

i. nitrous fumes generated with concentrated nitric acid and arsenic oxide;
ii. acetic acid plus concentrated nitric acid;
iii. fuming nitric acid in chloroform;
iv. concentrated nitric acid.

Since they are useful intermediates, the present invention includes compounds of formula IIA, except those which are known in the literature, that is compounds (IIA), provided that a. $R_1$, $R_2$, $R_3$, $R_4$ and $R_5$ are not all hydrogen;
b. $R_2$ is not a nitro group when $R_1$, $R_3$, $R_4$ and $R_5$ are all hydrogen; and
c. $R_2$ and $R_4$ are not both a nitro group when $R_1$, $R_3$ and $R_5$ are all hydrogen.

The starting materials of formula (II,$R_5$=H) may be prepared by standard methods known from the literature for the preparation of 4-hydroxycarbostyrils. For example the method of Patel and Mehta (*J. Sci. Ind. Research* 1960, 19B, 436–8) may be employed where an appropriately substituted aniline is condensed with diethyl malonate followed by hydrolysis of the monoanilide and cyclisation with polyphosphoric acid. With symmetrically substituted anilines or those substituted at one ortho position only one product results on cyclisation. With asymmetric anilines with both ortho positions free varying proportions of 5 -and 7-substituted hydroxy carbostyrils result. Thus with 3,4-dimethyl aniline a 1:1 mixture of the two possible isomers results. With bulkier substituents the ratio is influenced in favour of the newly formed C—C bond being furthest from the largest substituent (s). Thus 3,4-diethyl aniline results predominately in the 6,7-diethyl carbostyrils with only small amounts of the 5,6-diethyl isomer.

The starting materials of formula (II, $R_5$=alkyl aryl, or aralkyl) may be prepared from the appropriately substituted N-alkyl N-aryl or N-aralkyl, anthranilic acid by condensation with acetic anhydride in acetic acid. The N-alkyl anthranilic acids themselves are conveniently prepared by alkylation of the anthranilic acids with dialkyl sulphates under standard conditions. In these cases no isomeric products are obtained since the sites of new ring formation are already located.

The following Examples illustrate the preparation and properties of a number of compounds of formula (I):

EXAMPLE 1

4-Hydroxy-3-nitrocarbostyril

A suspension of 4-hydroxycarbostyril (1.5g; 0.0093 mole) in glacial acetic acid (10 ml) was well stirred during the addition of concentrated nitric acid (2.5 ml d, 1.42) and the mixture shaken at 95° C for a few minutes until dissolution was complete. The deep red solution soon deposited yellow crystals which after cooling were filtered off and washed with acetic acid and then ethanol. Drying in vacuo over phosphorus pentoxide afforded analytically pure 3-nitro compound m.p. 216° C (decomp) (Found C, 52.74; H, 3.14; N, 13.57; $C_9H_6N_2O_4$ required; C, 52.44; H, 2.93; N, 13.59%).

EXAMPLE 2

3,6-Dinitro-4-hydroxycarbostyril

Powdered potassium nitrate (3.2g, 0.038 mole) was added during 1 hr. to a stirred solution of 4-hydroxycarbostyril (2g 0.0124 mole) in concentrated sulphuric acid (20 ml) at 5° C. Concentrated nitric acid (4 ml, d 1.42) was than added portionwise and the mixture stirred at room temperature for 2½hrs. The yellow liquid was poured onto crushed ice and the yellow solid filtered and washed with a little cold water. Dissolution in hot dilute aqueous sodium carbonate afforded the yellow sodium salt on cooling. Acidification of an aqueous suspension of the sodium salt gave the free acid which had mp (AcOH) 199°–200° C (decomp). (Found; C, 42.95; H, ) 2.03; N, 16.79; $C_9H_5N_3O_6$ requires, C 43.04; H, 2.01 N, 16.73%).

The sodium salt was prepared by shaking a suspension of the dinitro compound in water with portions of 1N sodium hydroxide until a permanent alkaline pH was attained. The solid was filtered and washed well with water until the filtrate was neutral. Drying in vacuo over $P_2O_5$ at 98° gave analytically pure sodium salt. (Found; C,,39.64; H, 1.49; N, 15.26; $C_9H_4N_3NaO_6$ requires; C, 39.58; H, 1.48; N, 15.39%).

EXAMPLE 3

6-Chloro-4-hydroxy-3-nitrocarbostyril

A suspension of 6-chloro-4-hydroxycarbostyril (1.82g; 0.0093 mole) in glacial acetic acid (10 ml) was shaken with concentrated nitric acid (2.5 ml; d, 1.42) and the mixture heated on a water bath at 100° C until a clear solution resulted. Cooling of the orange solution gave a bright yellow solid which was filtered, washed well with acetic acid and then ethanol. Drying in vacuo over $P_2O_5$ NaOH gave analytically pure 6-chloro-4-hydroxy-3-nitrocarbostyril; decomposes 200° C. (Found: C, 45.31; H, 2.31 N, 11.93; Cl, 14.78; $C_9H_5N_2ClO_4$ requires; C, 44.93; H, 2.09; N, 11.64 Cl, 14.74%).

The sodium salt was prepared by treatment of the nitro derivative with 1 equivalent of aqueous sodium hydroxide with shaking and recrystallisation from water. (Found; C, 41,00; H, 1.60, Cl, 13.11, N, 10.75; Na, 9.48; $C_9H_4ClN_2NaO_4$ requires; C, 41.17; H, 1.54, Cl, 13.50, N, 10.67; Na 8.76%).

EXAMPLE 4

4-Hydroxy-6-methyl-3-nitrocarbostyril

A suspension of 4-hydroxy-6-methylcarbostyril (1.63g; 0.0093 mole) in glacial acetic acid (10 ml) was nitrated as described in example 3. The dried material, m.p. 239, was recrystallised from acetic acid/ethanol to give the title compound decomposing at 245° C. (Found; C, 54.51; H, 3.72; N, 13.13; $C_{10}H_8N_2O_4$ requires; C, 54.55; H, 3.66; N, 12.75%).

EXAMPLE 5

6-Ethyl-4-hydroxy-3-nitro-carbostyril

Concentrated nitric acid (2.5 ml, d, 1.42) was added to a stirred suspension of 6-ethyl-4-hydroxycarbostyril (1.76g; 0.0093 mole) and the mixture heated at 100° C until the initially clear, red solution deposited yellow crystals. After cooling the solid was filtered, washed with acetic acid and then ethanol and recrystallised. m.p. (AcOH) 220°–222° C. (Found; C, 56.67; H, 4.38; N, 11.64, $C_{11}H_{10}N_2O_4$ requires; C, 56.41; H, 4.30; N, 11.96%).

The sodium salt was prepared by dissolution of the free nitro compound in an equivalent of dilute aqueous sodium hydroxide and recrystallisation from water as a yellow solid. (Found, C, 49.98; H, 3.82; N, 10.73; Na 8.67, $C_{11}H_9N_2NaO_4 \cdot \frac{1}{2}H_2O$ requires; C, 49.82; H, 3.80; N, 10.56; Na 8.67%.

EXAMPLE 6

4-Hydroxy-5-methyl-3-nitrocarbostyril and 4-hydroxy-7-methyl-3-nitrocarbostyril Nitration of a 1:1 mixture of 4-hydroxy-5-methylcarbostyril and 4-hydroxy-7-methylcarbostyril (1.63g; 0.0093 mole) as described in Example 3 afforded a mixture of the two 3-nitro derivatives, m.p. 231°–232° C (Found, C, 54.18;H, 3.73; N, 12.87; $C_{10}H_8N_2O_4$ requires, C, 54.55; H, 3.66, N, 12.75%). Fractional recrystallisation from acetic acid gave the 5-methyl derivative m.p. 231° C (Found; C, 54.43; H, 3.71; N, 12.47; $C_{10}H_8N_2O_4$ requires; C, 54.55; H, 3.66; N, 12.75%) as the least soluble isomer and the 7-methyl derivative, m.p. 207°–210° C (Found, C, 54.03; H, 3.76; N, 12.25, $C_{10}H_8N_2O_5$ requires, C, 54.55; H, 3.66; N, 12.75%) as the more soluble isomer.

EXAMPLE 7

4-Hydroxy-8-methyl-3-nitrocarbostyril

A suspension of 4-hydroxy-8-methylcarbostyril (1.63g; 0.0093 mole), in glacial acetic acid (10 ml) was stirred during the addition of concentrated nitric acid (2.5 ml, d, 1.42) and the mixture warmed for 8 minutes at 100° C, after which time the solution had cleared and began to precipitate the yellow nitro derivative. After cooling, ethanol was added and the solid filtered and washed well with ethanol. On drying in vacuo over $P_2O_5$ NaOH it had m.p. 266°–267° C (Found: C, 54.41; H, 3.80; N, 12.51; $C_{10}H_8N_2O_4$ requires; C, 54.55; H, 3.66; N, 12.75%).

EXAMPLE 8

6-Bromo-4-hydroxy-3-nitrocarbostyril

A suspension of 6-bromo-4-hydroxycarbostyril (2.23g, 0.0093 mole) in glacial acetic acid (15 ml) was swirled during the addition of concentrated nitric acid (2.5 ml, d, 1.42). On heating at 100° C for several minutes a thick yellow solid separated. After cooling, ethanol (40 ml) was added and the mixture filtered and the solid washed free of nitric acid with ethanol. Drying in vacuo over $P_2O_5$ gave the title compound, m.p. 231°–4° C (d). (Found; C, 37.83; H, 1.74; N, 9.77; Br, 28.33; $C_9H_5N_2BrO_4$ requires; C, 37.92; H, 1.77; N, 9.83; Br, 28.03%).

Dissolution of the nitro compound in a slight excess of very dilute sodium hydroxide (ca O. OlN) followed by recrystallisation from the same gave the sodium salt as a yellow crystalline compound. Drying at 70°–90° C gave the anhydrous material as a very deliquescent solid (Found C, 34.72; H, 1.74 N, 8.92; $C_9H_4BrN_2NaO_4$ requires, C, 35.20, H, 1.31; N, 9.12%).

EXAMPLE 9

5,8-Dimethyl-4-hydroxy-3-nitrocarbostyril

A suspension of 5,8-dimethyl-4-hydroxycarbostyril (1.76g 0.0093 mole) in glacial acetic acid (10 ml) was stirred during the rapid addition of concentrated nitric acid (2.5 ml, d, 1.42). Heating on a steam bath for several minutes gave a yellow flocculent solid, which after cooling was diluted with ethanol, filtered and washed well with ethanol. Drying in vacuo over $P_2O_5$ gave the 3-nitro derivative, m.p. 270°–272° C (d). Found; C, 56.55;H, 4.33, N, 11.80; $C_{11}H_{10}N_2O_4$ requires; C, 56.41; H, 4.30, N, 11.96%).

EXAMPLE 10

5,7-Dimethyl-4-hydroxy-3-nitrocarbostyril

Nitration of 5,8-dimethyl-4-hydroxy carbostyril (1.76g; 0.0093 mole) as described in Example 9 gave 5,7-dimethyl-4-hydroxy-3-nitrocarbostyril as a yellow crystalline compound m.p. 226° C (d). . . (Found; C, 56.09 H, 4.30; N, 11.72; $C_{11}H_{10}N_2O_4$ requires; C, 56.41; H, 4.30 N, 11.96%).

EXAMPLE 11

6,8-Dimethyl-4-hydroxy-3-nitrocarbostyril

Concentrated nitric acid (2.5 ml; d, 1.42) was added rapidly to a suspension of 6,8-dimethyl-4-hydroxy carbostyril (1.76g — 0.0093 mole) in glacial acetic acid (10 ml) and the mixture warmed at 100° C until the yellow product separated. Filtration and recrystallization from acetic acid gave material of m.p. 290° (d). (Found; C, 56.41; H, 4.17; N, 11.94; $C_{11}H_{10}N_2O_4$ requires, C, 56.41; H, 4.30; N, 11.96%).

EXAMPLE 12

7,8-Dimethyl-4-hydroxy-3-nitrocarbostyril

Nitration of 7,8-dimethyl-4-hydroxy-carbostyril with concentrated nitric acid was described in Example 9 afforded the 3-nitro derivative, m.p. 284°–285° (d). (Found; C, 56.61; H, 4.30; N, 11.79; $C_{11}H_{10}N_2O_4$ requires; C, 56.41 H, 4.30; N, 11.96%).

EXAMPLE 13

8-Bromo-4-hydroxy-3-nitrocarbostyril

To a suspension of 8-bromo-4-hydroxycarbostyril (2.23g; 0.0093 mole) in glacial acetic acid (10 ml) was added concentrated nitric acid (2.5 ml; d, 1.42) and the mixture heated on a steam bath until the yellow 3-nitro derivative separated. Ethanol was added to the cooled mixture and the filtered product washed well with ethanol and dried in vacuo over $P_2O_5$/NaOH m.p. 191° (d); (Found; C, 38.24; H, 1.91; N, 9.65; Br, 27.97; $C_9H_5BrN_2O_4$ requires; C, 37.92; H, 1.77; N, 9.83; Br, 28.03%).

A suspension of the nitro compound in water was treated with 1 equivalent of dilute sodium hydroxide solution and the yellow sodium salt recrystallised from water (Found; C, 35.86; 1.51; N, 9.37; Br, 26.42; Na, 7.09; $C_9H_4BrN_2NaO$ requires; C, 35.20; H, 1.31; N, 9.12; Br, 26.03; Na, 7.49%).

EXAMPLE 14

8-Chloro-4-hydroxy-3-nitrocarbostyril

A suspension of 8-chloro-4-hydroxycarbostyril (1.82g. 0.0093 mole) in glacial acetic acid (10 ml) was nitrated as described in Example 13 to afford the 3-nitro derivative, m.p. 200°–202° (d). (Found, C, 44.92; H, 2.27; N, 11.58; Cl, 14.68; $C_9H_5N_2ClO_4$ requires; C, 44.93; H, 2.09; N, 11.64; Cl, 14.74%).

EXAMPLE 15

6,7-Dimethyl-4-hydroxy-3-nitrocarbostyril

Nitration of a 1:1 mixture of 5,6-dimethyl-4-hydroxycarbostyril and 6,7-dimethyl-4-hydroxy-carbostyril as described in Example 3 afforded a mixture of the 3-nitro derivatives from which the 6,7-dimethyl isomer was isolated as the more soluble isomer by fractional crystallisation from acetic acid; m.p. 221°–225° (Found; C, 56.46; H, 4.51 N, 11.86; $C_{11}H_{10}N_2O_4$ requires; C, 56.41; H, 4.30; N, 11.86%).

EXAMPLE 16

7-Chloro-4-hydroxy-3-nitrocarbostyril

A suspension of 7-chloro-4-hydroxycarbostyril (0.5g.) in glacial acetic acid (4 ml.) was nitrated with concentrated nitric acid (0.7ml.) at 100° C and worked up in the usual manner to give the title compound, m.p. (aqueous ethanol) 166° – 167° C.

EXAMPLE 17

(a) Malonic acid mono (3,4-diethyl) anilide

A mixture of 3,4-diethyl aniline 39.0g; 0.263 mole) and diethyl malonate (73.2g.; 0.458 mole) was gently refluxed for 45 minutes., the ethanol formed being removed via an insulated 5 inch air column. After cooling and addition of twice its volume of ethanol the precipitated diamide was filtered off and the filtrate steam distilled during 1 hr. in the presence of a solution of sodium carbonate (40g) in water (350 ml.). The flask contents were cooled, filtered to remove residual amide, and the mono anilide precipitated with concentrated hydrochloric acid, m.p. (water) 120° – 121° C (Found: C, 65.97; H, 7.29; N, 5.89; $C_{13}H_{17}NO_3$ requires; C, 66.36; H, 7.28; N, 5.95%)

(b) 6,7-Diethyl-4-hydroxycarbostyril

A solution of malonic acid mono (3,4-diethyl) analide (54g.; 0.23 mole) in polyphosphoric acid (from phosphorus pentoxide (230g.) in syrupy phosphoric acid (140 ml.) was stirred at 140° C for 3 hr., cooled and 1N hydrochloric acid (690 ml.) added. After bringing the pH to 4 with 10% sodium hydroxide solution the hydroxy carbostyril was filtered off, washed well with water and recrystallised from glacial acetic acid. It had a m.p. > 300° C (Found; C, 71.69; H, 6.88; N, 6.26; $C_{13}H_{15}NO_2$ requires; C, 71.87; H, 6.96; N, 6.45%) and the nmr showed small traces of the 5,6-diethyl isomer.

(c) 6,7-Diethyl-4-hydroxy-3-nitrocarbostyril

Nitration of 6,7-diethyl-4-hydroxycarbostyril (3.9g.; 0.018 mole) as previously described gave the 3-nitro derivative as a yellow crystalline solid, m.p. (EtOH) 248° – 250° C (d). (Found; C, 59.28; H, 5.60; H, 10.56; $C_{13}H_{14}N_2O_4$ requires; C, 59.53; H, 5.38; N, 10.68%). The nmr showed no 5,6-diethyl isomer.

By nitrating the following starting materials in glacial acetic acid with concentrated nitric acid using the same general procedure as in Example 1:

4-hydroxy-7-methoxy carbostyril;
4-hydroxy-7-methoxy-6-methyl carbostyril;
8-ethoxy-4-hydroxy-6-n-propyl carbostyril;
4-hydroxy-7-methyl-8-n-propoxy carbostyril;
4-hydroxy-7-phenoxy carbostyril;
7-Benzyloxy-4-hydroxy-6-methyl carbostyril;
7-ethyl-4-hydroxy-6-phenyl carbostyril;
8-Benzyl-4-hydroxy-6-methyl carbostyril;
4-hydroxy-6-methyl-7-(3'-pyridyl) carbostyril;
4-hydroxy-8-(3'-pyridyl) carbostyril;
4,7-dihydroxycarbostyril;
4-hydroxy-7-n-propoxy carbostyril;
the following compounds are obtained:

| Ex. No. | |
|---|---|
| 18. | 4-hydroxy-7-methoxy-3-nitrocarbostyril; |
| 19. | 4-hydroxy-7-methoxy-6-methyl-3-nitrocarbostyril; |
| 20. | 8-ethoxy-4-hydroxy-3-nitro-6-n-propyl carbostyril; |
| 21. | 4-hydroxy-7-methyl-8-n-propoxy-3-nitrocarbostyril; |
| 22. | 4-hydroxy-3-nitro-7-phenoxy carbostyril; |
| 23. | 7-benzyloxy-4-hydroxy-6-methyl-3-nitrocarbostyril; |
| 24. | 7-ethyl-4-hydroxy 3-nitro-6-phenyl carbostyril; |
| 25. | 8-benzyl-4-hydroxy-6-methyl-3-nitrocarbostyril; |
| 26. | 4-hydroxy-6-methyl-3-nitro-7-(3'-pyridyl) carbostyril; |
| 27. | 4-hydroxy-3-nitro-8-(3'-pyridyl)carbostyril; |
| 28. | 4,7-dihydroxy-3-nitro-carbostyril; |
| 29. | 4-hydroxy-3-nitro-7-n-propoxy carbostyril. |

EXAMPLE 30

(a) 1-Ethyl-4-hydroxy carbostyril

A solution of N-ethyl anthranilic acid (12.0g; 0.073 mole) in acetic acid (37 ml) and acetic anhydride (37ml) was refluxed for 4 hrs. The red solution was cooled, poured onto crushed ice and made alkaline with aqueous sodium hydroxide. After filtering the yellow filtrate was neutralised with concentrated hydrochloric acid (pH 5) and the yellow solid filtered and washed with water. Recrystallisation from acetic acid in the presence of charcoal gave the title compound as an orange solid, m.p. 273°–275° C. (Found: C, 69.85; H, 6.04; N, 7.29; $C_{11}H_{11}NO_2$ requires: C, 69.83; H, 5.86; N, 7.40%).

(b) 1-Ethyl-4-hydroxy-3-nitro carbostyril

A suspension of 1-ethyl-4-hydroxy carbostyril (1.09 g; 0.00575 mole) in glacial acetic acid (5 ml) was swirled during the rapid addition of concentrated nitric acid (1.25 ml; d 1.42) and the dark liquid heated for 5 minutes at 100° C. The yellow solid which separated on cooling was filtered off and washed well with ethanol m.p. 154°–5° C (decomp). (Found; C, 56.54; H, 4.52; N, 11.56; $C_{11}H_{10}N_2O_4$ requires; C, 56.41; H, 4.30, N, 11.96%).

EXAMPLE 31

(a) 4-Hydroxy-1-methyl carbostyril

This was prepared from N-methyl anthranilic acid (22.04g. 0.146 mole) as described in Example 30a., m.p. (EtOH) 270°–273° C. (Found; C, 68.59; H, 5.44; N, 7.73; $C_{10}H_9NO_2$ requires; C, 58.56; H, 5.18; N, 8.00%).

(b) 4-Hydroxy-1-methyl-3-nitro carbostyril

A suspension of 4-hydroxy-1-methyl carbostyril (1.63g; 0.009 mole) in glacial acetic acid (10 ml) was stirred during the addition of concentrated nitric acid (2.5 ml; d, 1.42) and the mixture heated for a few minutes on a steam bath. On cooling the clear red solution deposited yellow crystals of the title compound which were diluted with ethanol, filtered, and washed well with ethanol, m.p. 159°–161° C (Found: C, 54.20; H 3.71; N, 12.42; $C_{10}H_8N_2O_4$ requires; C, 54.55 H, 3.66; N, 12.72%).

EXAMPLE 32

(a) 1,6-Dimethyl-4-hydroxy carbostyril

Reaction of N,5-Dimethyl anthranilic acid (19g; 0.115 mole) in acetic acid (58 ml) and acetic anhydride (58 ml) as described in Example 30a, afforded the title compound; m.p. (EtOH) 290°–298° C (Found; C, 70.16; H, 6.15; N, 7.04; $C_{11}H_{11}NO_2$ requires; C, 69.88; H, 5.86; N, 7.40%).

(b) 1,6-Dimethyl-4-hydroxy-3-nitro carbostyril

To a stirred suspension of 1,6-dimethyl-4-hydroxy carbostyril (1.70g; 0.009 mole) in glacial acetic acid (10 ml) was added concentrated nitric acid (2.5 ml; d, 1.42) with swirling. The solid dissolved on warming to 100° C to give a red solution which precipitated the 3-nitro compound as yellow crystals on cooling. m.p. 185° C. (Found; C, 56.05; H, 4.33; N, 11.86%, $C_{11}H_{10}N_2O_4$ requires; C, 56.41; H, 4.30; N, 11.96%).

EXAMPLE 33

(a) 1-Ethyl-4-hydroxy-6-methyl carbostyril

N-Ethyl-5-methyl anthranilic acid (17.6g — 0.098 mole; m.p. 159° C) was refluxed in acetic acid (43 ml) and acetic anhydride (43 ml) for 12 hrs. The dark red solution was cooled and poured onto crushed ice. The mixture was made alkaline, filtered off tarry material and neutralised with hydrochloric acid. The yellow crystalline product was filtered off, washed well with water and recrystallised from ethanol, m.p. 275°–280° (Found- C, 70,87; H, 6.34; N, 7.17 $C_{12}H_{13}NO_2$ requires; C, 70.88; H, 6.44; N, 6.89%).

(b) 1-Ethyl-4-hydroxy-6-methyl-3-nitro carbostyril

Concentrated nitric acid (2.5 ml; d, 1.42) was added to a suspension of 1-ethyl-4-hydroxy-6-methyl carbostyril. (1.82g; 0.009 mole) in glacial acetic acid (10 ml) and the mixture warmed to 100° C. The solid dissolved and the 3-nitro derivative immediately solidified as a yellow solid. After cooling the solid was filtered, washed well with water and dried in vacuo over $P_2O_5$, m.p. 192°–4° C; (Found; C, 58.16; H, 5.02; N, 11.29; $C_{12}H_{12}N_2O_4$ requires; C, 58.06; H, 4.87; N, 11.29%).

EXAMPLE 34

(a) 6-Chloro-4-Hydroxy-1-methyl carbostyril

5-Chloro-N-methyl anthranilic acid (15g; 0.081 mole) was dissolved in acetic acid (41 ml) and acetic anhydride (41 ml) and the dark mixture refluxed for 12 hours. After cooling the red solution was poured onto crushed ice, basified with 2.5N sodium hydroxide and filtered free of tar. The filtrate on acidification to pH5 gave the carbostyril as a yellow solid, m.p. (AcOH) 317°–318° C (Found; C, 57.39; H, 3.98; N, 6.83; Cl, 16.69; $C_{10}H_8NClO_2$ requires C, 57.29; H, 3.85; N, 6.68; Cl, 16.91%).

(b) 6-Chloro-4-hydroxy-1-methyl-3-nitro carbostyril

A suspension of 6-chloro-4-hydroxy-1-methyl carbostyril (1.0g; 0.0048 mole) in glacial acetic acid (5 ml) was treated with concentrated nitric acid (1.25 ml — d 1.42) and heated to 100° C for 2 minutes. The red solution was cooled to give a yellow solid. Dilution with ethanol followed by filtration and washing with ethanol afforded the 3-nitro derivative, m.p. 171° C (d). (Found: C, 46.85; H, 2.86; N, 10.96; Cl, 13.78; $C_{10}H_7N_2ClO_4$ requires: C, 47.17; H, 2.77; N, 11.00; Cl, 13.92%).

The sodium salt was prepared by dissolution of the free nitro compound in a slight excess of dilute sodium hydroxide and recrystallisation from the same. It forms a yellow highly crystalline, hygroscopic solid, (Found: C, 43.57; H, 2.32; N, 10.04; Cl, 12.84; N, 10.13; Cl, 12.82; Na, 8.31%).

EXAMPLE 35

(a) 6-Chloro-1-ethyl-4-hydroxy carbostyril

5-Chloro-N-ethyl anthranilic acid (13.1g; 0.006 mole) in acetic acid (35 ml) and acetic anhydride (35 ml) was refluxed for 24 hours. The cooled mixture was poured into ice-water and basified to pH 14. The precipitated red oil was separated and the supernatant acidified to pH 5 to give the title compound as a white crystalline solid. m.p. (EtOH) 305°–8° C (Found: C, 58.80; H, 4.64; N, 6.49; Cl, 15.95; $C_{11}H_{10}ClNO_2$ requires, C, 59.07; H, 4.51; N, 6.26; Cl, 15.85%).

(b) 6-Chloro-1-ethyl-4-hydroxy-3-nitro carbostyril

Nitration of a suspension of 6-chloro-1-ethyl-4-hydroxy carbostyril (1.66g; 0.0074 mole) as described in Example 30 (b) afforded the 3-nitro derivative; m.p. (AcOH) 205°–6° (d) (Found: C, 49.91; H, 3.59; N, 9.79; Cl, 13.35; $C_{11}H_9N_2ClO_4$ requires: C, 49.18; H, 3.38; N, 10.43; Cl, 13.20%).

EXAMPLE 36

(a) 7-Chloro-4-hydroxy-1-methyl carbostyril

Refluxing a solution of 4-chloro-N-methyl anthranilic acid (13.6g; 0.073 mole) in acetic acid (37 ml) and acetic anhydride (37 ml) for 6 hours and work up as described in Example 35(a) gave the title compound; m.p. (AcOH, EtOH) 308°–9°. (Found; C, 56.97; H, 4.03; N, 6.89 Cl, 16.82; $C_{10}H_8NClO_2$ requires; C, 57.29; H, 3.85; N, 6.68; Cl, 16.91%).

(b) 7-Chloro-4-hydroxy-1-methyl-3-nitro carbostyril

A suspension of 7-chloro-4-hydroxy-1-methyl carbostyril (1.0g; 0.0048 mole) in glacial acetic acid (5 ml) was treated with concentrated nitric acid (1.25 ml; d 1.42) and the mixture heated for 2 minutes at 100° C. Filtration of the dark green solution followed by cooling and dilution with ethanol gave the 3-nitro derivative as a yellow solid; m.p. 164°–5° (d). (Found: C, 46.80; H, 2.79; N, 10.99; Cl, 13.68; $C_{10}H_7N_2ClO_4$ requires; C, 47.17; H, 2.77; N, 11.00; Cl, 13.92%).

EXAMPLE 37

(a) 4-Hydroxy-1-phenyl carbostyril

A solution of N-phenyl anthranilic acid (30.1g.; 0.146 mole) and acetic anhydride (74 ml.) in glacial acetic acid (74 ml.) was refluxed for 4 hrs. The resulting red solution was cooled, poured onto crushed ice-water (600 ml) and brought to pH 9 with dilute sodium hydroxide solution. After filtration the clear liquid was taken to pH 5 with hydrochloric acid and the white solid filtered off and dried, m.p. (AcOH) 298°–300° C. (Found: C, 75.40; H, 4.58; N, 5.70; $C_{15}H_{11}NO_2$ requires; C, 75.94; H, 4.67; N, 5.90%).

(b) 4-Hydroxy-3-nitro-1-phenylcarbostyril

A solution of 4-hydroxy-1-phenyl carbostyril (2.20g.; 0.0093 mole) in glacial acetic acid (10 ml.) was treated rapidly with concentrated nitric acid (2.5 ml. d 1.42) and the mixture heated on a steam bath for 2½ mins. The red solution deposited a dark yellow solid on cooling which, after dilution with ethanol, was filtered off and washed well with ethanol, m.p. (AcOH — EtOH) 167° – 169° C. (Found; C, 64.13; H, 3.70; N, 9.85; $C_{15}H_{10}N_2O_4$ requires; C, 63.83; H, 3.57; N, 9.92%).

EXAMPLE 38

(a) 4-Hydroxy-1,6,7-trimethyl carbostyril

To a solution of 4,5-dimethyl-N-methyl anthranilic acid (30.0g.; 0.168 mole; m.p. 190° – 191° C) in glacial acetic acid (75 ml.) was added acetic anhydride (75 ml.) and the mixture was refluxed for 4 hrs. After cooling the dark solution was poured onto crushed ice, made alkaline (pH 9), and filtered. On bringing the filtrate to pH5 with concentrated hydrochloric acid the title product separated as a white solid, m.p. (EtOH) 300° – 305° C (Found: C, 70.12; H, 6.30; N, 7.12; $C_{12}H_{13}NO_2$ requires; C, 70.92; H, 6.45; N, 6.89%).

(b) 4-Hydroxy-3-nitro-1,6,7-trimethylcarbostyril

Nitration of 4-hydroxy-1,6,7-trimethyl carbostyril (1.8g.; 0.009 mole) as described in Example 37 (b) yielded the 3-nitro derivative, m.p. (EtOH) 220° – 224° C (d). (Found; C, 58.15; H, 5.03; N, 11.34; $C_{12}H_{12}N_2O_4$ requires C, 58.06; H, 4.87; N, 11.29%).

Following the general procedure of Example 30(a) using the corresponding substituted anthranilic acid, the following intermediates are prepared:
1-benzyl-4-hydroxycarbostyril;
6-ethyl-4-hydroxy-7-methoxy-1-methyl carbostyril
1,7-dimethyl-4-hydroxy-6-methoxy carbostyril
7-chloro-4-hydroxy-6-methoxy carbostyril
6-chloro-1,8-dimethyl-7-ethoxy-4-hydroxy carbostyril
6,7-dimethoxy-4-hydroxy-1-methyl-carbostyril
7-benzyloxy-4-hydroxy-1-methyl carbostyril
4-hydroxy-1-methyl-7-phenoxy carbostyril
4-hydroxy-1-methyl-6-phenyl carbostyril
6-benzyl-1-ethyl-4-hydroxy carbostyril
4-hydroxy-1-methyl-6-(3'-pyridyl)-carbostyril
4-hydroxy-1-methyl-7-(3'-pyridyl)-carbostyril
4,7-dihydroxy-1-ethyl-6-methyl carbostyril
4-hydroxy-1-methyl-6-nitro carbostyril
6,7-diethyl-4-hydroxy-1-methyl carbostyril
4-hydroxy-1,7,8-trimethyl carbostyril
1,8-dimethyl-4-hydroxy carbostyril
6-ethyl-4-hydroxy-1-methyl carbostyril
and are converted into the following nitrocarbostyrils using the general procedure of Example 30 (b):

| Ex. No. | |
|---|---|
| 39 | 1-benzyl-4-hydroxy-3-nitrocarbostyril; |
| 40 | 6-ethyl-4-hydroxy-7-methoxy-1-methyl-3-nitrocarbostyril |
| 41 | 1,7-dimethyl-4-hydroxy-6-methoxy-3-nitro carbostyril |
| 42 | 7-chloro-4-hydroxy-6-methoxy-3-nitro carbostyril |
| 43 | 6-chloro-1,8-dimethyl-7-ethoxy-4-hydroxy-3-nitro carbostyril |
| 44 | 6,7-dimethoxy-4-hydroxy-1-methyl-3-nitro carbostyril |
| 45 | 7-benzyloxy-4-hydroxy-1-methyl-3-nitro carbostyril |
| 46 | 4-hydroxy-1-methyl-3-nitro-7-phenoxy carbostyril |
| 47 | 4-hydroxy-1-methyl-3-nitro-6-phenyl-carbostyril |
| 48 | 6-benzyl-1-ethyl-4-hydroxy-3-nitro carbostyril |
| 49 | 4-hydroxy-1-methyl-3-nitro-6-(3'-pyridyl) carbostyril |
| 50 | 4-hydroxy-1-methyl-3-nitro-7-(3'-pyridyl) carbostyril |
| 51 | 4,7-dihydroxy-1-ethyl-6-methyl-3-nitro carbostyril |
| 52 | 3,6-dinitro 4-hydroxy-1-methyl carbostyril |
| 53 | 6,7-diethyl-4-hydroxy-1-methyl-3-nitrocarbostyril; |
| 54 | 4-hydroxy-3-nitro-1,7,8-trimethyl-carbostyril; |
| 55 | 1,8-dimethyl-4-hydroxy-3-nitrocarbostyril; |
| 56 | 6-ethyl-4-hydroxy-1-methyl-3-nitrocarbostyril. |

EXAMPLE 57

Some of the 4-hydroxycarbostyrils prepared in the preceding examples were tested in the rat Passive Cutaneous Anaphylaxis Test (PCA test), described below. They were administered as their sodium salts either in pH 7.2 phosphate buffer (for soluble salts) or as a suspension in 1% methyl cellulose (for insoluble salts).

i. Serum containing heat labile homocytotropic antibody was raised in rats by a method similar to that used by Mota. I. Mota Immunology 1964, 7, 681).

Male Wistar rats of 250–300g, were injected intraperitoneally with 0.5 ml. of *Bordatella pertussis* vaccine (containing 4 × 10¹⁰ dead organism per ml) and subcutaneously with 0.5 ml. of an emulsion of 100 mg. of ovalbumin in 2 ml. of saline and 3 ml. of incomplete Freunds' adjuvant. Rats were bled by cardiac puncture on day 18, the blood was pooled and separated and serum stored at −20° and thawed only once before use.

ii. The P.C.A. test was similar to that described by Ovary and Bier (A. Ovary and O. E. Bier, Prod. Soc. Exp. Biol. Med. 1952, 81, 584) and Goose and Blair (J. Goose and A.M.J.N. Blair, Immunology 1969, 16, 769).

0.1 ml. of each of six twofold serial dilutions of the serum in 0.9% saline were injected intradermally into separate sites on the shaved dorsal surface of 250–350 g. Male Wistar rats. 72 hours later the animals were challenged by i.v. injection of 0.3 ml. of 1% ovalbumin mixed with 0.1 ml. of a 5% solution of pontamine sky blue dye both in isotonic saline buffered with pH. 7.2 Sorenson buffer (P.P.S.). The rats were killed after 20 minutes and the diameter of the blue wheals at the antibody injection sites were measured. The starting dilution of the serum was adjusted so that there was no response after challenge, at the site of injection of the highest dilution and a maximum response at the two or three lowest dilutions. Typically, six twofold serial dilutions of the serum ¼ to 1ω128 were used.

Compounds were tested for their ability to reduce the diameter of the wheals at the injection sites of dilutions of antibody which on all the controls have less than maximum response. Amounts of the compounds were administered to rats by subcutaneous injection, into the nucal region, of a solution of the compound in P.B.S. or as a suspension in 1% methyl cellulose, each amount to a test group of six animals at a specified time prior to intravenous challenge with ovalbumin. The diameters of the blue wheals which developed on the test group of animals were compared with those on a control group of six animals treated in the same way as the test group, but which had received an equivalent subcutaneous injection of the carrier fluid of the same volume but not containing the compound under test.

% Inhibition of P.C.A. = 100 (1 − a/b)

a = The mean of the sum of the diameters of the wheals produced in the test group of animals at those antibody sites where all the control group of animals gave less than maximum response.

= The mean of the sum of diameters of the wheals produced in the control group of animals at those antibody sites where all the animals in group gave less than maximum response.

The preferred method of administration was a solution of the test compound dissolved in pH 7.2 buffer and neutralised with sodium bicarbonate. For those compounds having insoluble sodium salts, the salts were isolated by reaction of the free nitro compound with 2.5N sodium hydroxide and the filtered sodium salt washed free of alkalyl with water. The dried salts were then administered as a suspension in 1% methyl cellulose.

BIOLOGICAL RESULTS

| | dose (mg/Kg) | time (mins.) | % inhibition of PCA response |
|---|---|---|---|
| Example 1 | | | |
| | 25 | 0 | 9 |
| | 100 | 0 | 33 |
| | 25 | 30 | 19 |
| | 100 | 30 | 40 |
| Example 2 | | | |
| | 25 | 0 | 4 |
| | 100 | 0 | −14 |
| | 25 | 60 | 31 |
| | 100 | 60 | 23 |
| Example 3 | | | |
| | 25 | 0 | −39 |
| | 100 | 0 | −30 |
| | 25 | 60 | 33 |
| | 100 | 60 | 54 |
| Example 4 | | | |
| | 25 | 0 | 14 |
| | 100 | 0 | 30 |
| | 25 | 60 | 15 |
| | 100 | 60 | 23 |
| Example 5 | | | |
| | 25 | 0 | 19 |
| | 100 | 0 | 26 |
| | 25 | 60 | 13 |
| | 100 | 60 | 33 |
| Example 6 (a) | | | |
| | 25 | 0 | 5 |
| | 100 | 0 | 7 |
| | 25 | 60 | 1 |
| | 100 | 60 | 51 |
| (b) | 25 | 0 | 12 |
| | 100 | 0 | 7 |
| | 25 | 60 | 1 |
| | 100 | 60 | 23 |
| Example 7 | | | |
| | 25 | 0 | 23 |
| | 100 | 0 | 71 |
| | 25 | 30 | 18 |
| | 100 | 30 | 36 |
| Example 8 | | | |
| | 25 | 0 | 5 |
| | 100 | 0 | −11 |
| | 25 | 60 | 25 |
| | 100 | 60 | 19 |
| Example 9 | | | |
| | 25 | 0 | 7 |
| | 100 | 0 | 22 |
| | 25 | 30 | 9 |
| | 100 | 30 | 27 |
| Example 10 | | | |
| | 25 | 0 | 0 |
| | 100 | 0 | 22 |
| | 25 | 60 | 35 |
| | 100 | 60 | 44 |
| Example 11 | | | |

-continued
BIOLOGICAL RESULTS

| | dose (mg/Kg) | time (mins.) | % inhibition of PCA response |
|---|---|---|---|
| | 25 | 0 | 11 |
| | 100 | 0 | 0 |
| | 25 | 60 | 52 |
| | 100 | 60 | 51 |
| Example 12 | | | |
| | 25 | 0 | 9 |
| | 100 | 0 | 50 |
| | 25 | 30 | 36 |
| | 100 | 30 | 47 |
| Example 13 | | | |
| | 25 | 0 | 36 |
| | 100 | 0 | 49 |
| | 25 | 60 | 32 |
| | 100 | 60 | 32 |
| Example 14 | | | |
| | 25 | 0 | 18 |
| | 100 | 0 | 26 |
| | 25 | 60 | 42 |
| | 100 | 60 | 43 |
| Example 15 | | | |
| | 25 | 0 | 62 |
| | 100 | 0 | 88 |
| | 25 | 60 | 27 |
| | 100 | 60 | 54 |
| Example 16 | | | |
| | 25 | 0 | −3 |
| | 100 | 0 | 13 |
| | 25 | 30 | 9 |
| | 100 | 30 | 63 |
| Example 17 | | | |
| | 25 | 0 | 25 |
| | 100 | 0 | 32 |
| | 25 | 60 | 34 |
| | 100 | 60 | 42 |
| Example 30 | | | |
| | 25 | 0 | 9 |
| | 100 | 0 | 20 |
| | 25 | 30 | 34 |
| | 100 | 30 | 41 |
| Example 31 | | | |
| | 25 | 0 | 21 |
| | 100 | 0 | 35 |
| | 25 | 30 | 26 |
| | 100 | 30 | 36 |
| Example 32 | | | |
| | 25 | 0 | −12 |
| | 100 | 0 | 16 |
| | 25 | 30 | 55 |
| | 100 | 30 | 26 |
| Example 33 | | | |
| | 25 | 0 | −12 |
| | 100 | 0 | −1 |
| | 25 | 60 | −5 |
| | 100 | 60 | 16 |
| Example 34 | | | |
| | 25 | 0 | −5 |
| | 100 | 0 | 43 |
| | 25 | 60 | 8 |
| | 100 | 60 | 61 |
| Example 35 | | | |
| | 25 | 0 | 8 |
| | 100 | 0 | 5 |
| | 25 | 60 | 11 |
| | 100 | 60 | 88 |
| Example 36 | | | |
| | 25 | 0 | −4 |
| | 100 | 0 | 34 |
| | 25 | 60 | −2 |
| | 100 | 60 | 50 |
| Example 37 | | | |
| | 25 | 0 | −2 |
| | 100 | 0 | 13 |
| | 25 | 30 | 1 |
| | 100 | 30 | 42 |
| Example 38 | | | |
| | 25 | 0 | 13 |
| | 100 | 0 | 53 |
| | 25 | 30 | 14 |
| | 100 | 30 | 47 |

We claim:
1. A compound of the formula (IA) or a pharmaceutically acceptable salt thereof:

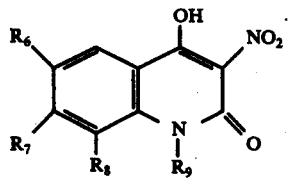 (IA)

wherein one of the groups $R_6$, $R_7$ and $R_8$ are hydrogen and the other two are methyl, ethyl, n-propyl, methoxy, ethoxy or n-propoxy, and $R_9$ is hydrogen or lower alkyl.

2. The compound 6,7-dimethyl-4-hydroxy-3-nitro-carbostyril or a pharmaceutically acceptable salt thereof.

3. The compound 1,6,7-trimethyl-4-hydroxy-3-nitro-carbostyril or a pharmaceutically acceptable salt thereof.

4. The compound 6,7-diethyl-4-hydroxy-3-nitro-carbostyril or a pharmaceutically acceptable salt thereof.

5. The compound 7,8-dimethyl-4-hydroxy-3-nitro-carbostyril or a pharmaceutically acceptable salt thereof.

6. The compound 8-methyl-4-hydroxy-3-nitro-carbostyril or a pharmaceutically acceptable salt thereof.

* * * * *